US010117684B2

(12) United States Patent
Saidha et al.

(10) Patent No.: US 10,117,684 B2
(45) Date of Patent: Nov. 6, 2018

(54) PUSH-OFF DRIVER AND METHOD FOR INSERTING BONE SCREWS

(71) Applicant: DePuy Synthes Products, Inc., Raynham, MA (US)

(72) Inventors: Sean Saidha, East Fallowfield, PA (US); William Strausbaugh, Leola, PA (US); Boyd A. Wolf, Coatsville, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/896,599

(22) Filed: Feb. 14, 2018

(65) Prior Publication Data

US 2018/0235674 A1 Aug. 23, 2018

Related U.S. Application Data

(63) Continuation of application No. 15/384,803, filed on Dec. 20, 2016, now Pat. No. 9,924,980, which is a
(Continued)

(51) Int. Cl.
*A61B 17/58* (2006.01)
*A61B 17/60* (2006.01)
(Continued)

(52) U.S. Cl.
CPC ...... *A61B 17/7082* (2013.01); *A61B 17/7032* (2013.01); *A61B 17/7035* (2013.01);
(Continued)

(58) Field of Classification Search
None
See application file for complete search history.

(56) References Cited

U.S. PATENT DOCUMENTS 4,763,548 A 8/1988 Leibinger et al.
6,299,616 B1 10/2001 Beger
(Continued)

FOREIGN PATENT DOCUMENTS

DE 8531467 5/1986
DE 29819914 1/1999
(Continued)

OTHER PUBLICATIONS

Extended European Search Report, dated Aug. 5, 2014, received in connection with corresponding European Application No. 14001106.5.
(Continued)

*Primary Examiner* — Sameh Boles
(74) *Attorney, Agent, or Firm* — Meunier Carlin & Curfman LLC

(57) ABSTRACT

A method and device for inserting screws into a patient, such that when the device is removed the device does not stick to the screw. The device, being a push-off driver, may have a handle, an inner driver, and a threaded driver sleeve having a button mechanism and a plurality of spheres, and an inner sleeve. The method includes the steps of assembling a push-off driver attaching a bone screw to the push-off driver inserting the bone screw and detaching the bone screw from the driver by unthreading the threaded driver sleeve from the polyaxial screw which causes the spheres in the recess of the inner driver to back up against the start of the recess and causing the threaded driver sleeve to "push-off" the polyaxial screw from the inner driver.

20 Claims, 11 Drawing Sheets

Related U.S. Application Data continuation of application No. 14/617,397, filed on Feb. 9, 2015, now Pat. No. 9,554,834, which is a continuation of application No. 13/888,509, filed on May 7, 2013, now Pat. No. 8,951,264, which is a continuation of application No. 11/840,638, filed on Aug. 17, 2007, now Pat. No. 8,460,307.

(60) Provisional application No. 60/838,797, filed on Aug. 17, 2006.

(51) Int. Cl.
*A61F 2/00* (2006.01)
*A61B 17/70* (2006.01)
*B25B 23/10* (2006.01)
*A61B 17/86* (2006.01)
*A61B 17/00* (2006.01)

(52) U.S. Cl.
CPC ........ *A61B 17/862* (2013.01); *A61B 17/8615* (2013.01); *B25B 23/101* (2013.01); *A61B 2017/00407* (2013.01)

(56) References Cited

U.S. PATENT DOCUMENTS 6,981,976 B1  1/2006  Schoenefeld

| 2002/0020255 | A1 | 2/2002 | Simon et al. |
|---|---|---|---|
| 2003/0199983 | A1 | 10/2003 | Michelson |
| 2004/0225292 | A1 | 11/2004 | Sasso et al. |
| 2005/0209592 | A1 | 9/2005 | Schlapfer et al. |
| 2005/0216027 | A1 | 9/2005 | Suh et al. |
| 2006/0111712 | A1 | 5/2006 | Jackson |
| 2006/0241622 | A1 | 10/2006 | Zergiebel |
| 2007/0043378 | A1* | 2/2007 | Kumar ............... A61B 17/7082 606/104 |
| 2008/0045970 | A1 | 2/2008 | Saidha et al. |

FOREIGN PATENT DOCUMENTS

| JP | 09001432 | 1/1997 |
|---|---|---|
| JP | 2001017440 | 1/2001 |
| JP | 5237282 | 7/2013 |
| SU | 827050 | 5/1981 |
| WO | 2005/099601 | 10/2005 |
| WO | 2008/022318 | 2/2008 |

OTHER PUBLICATIONS

International Preliminary Report on Patentability and Written Opinion, dated Feb. 17, 2009, in corresponding International Application No. PCT/US2007/076217.

International Search Report, dated Feb. 26, 2008, in corresponding International Application No. PCT/US2007/076217.

* cited by examiner

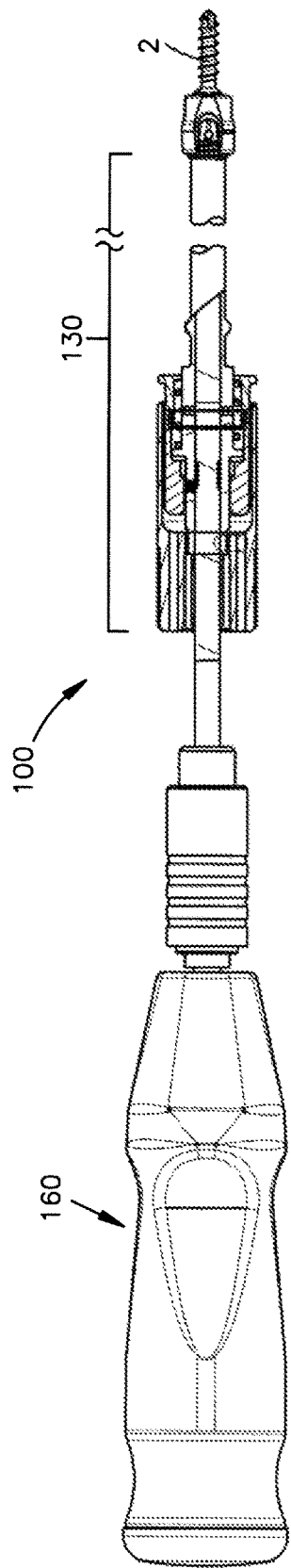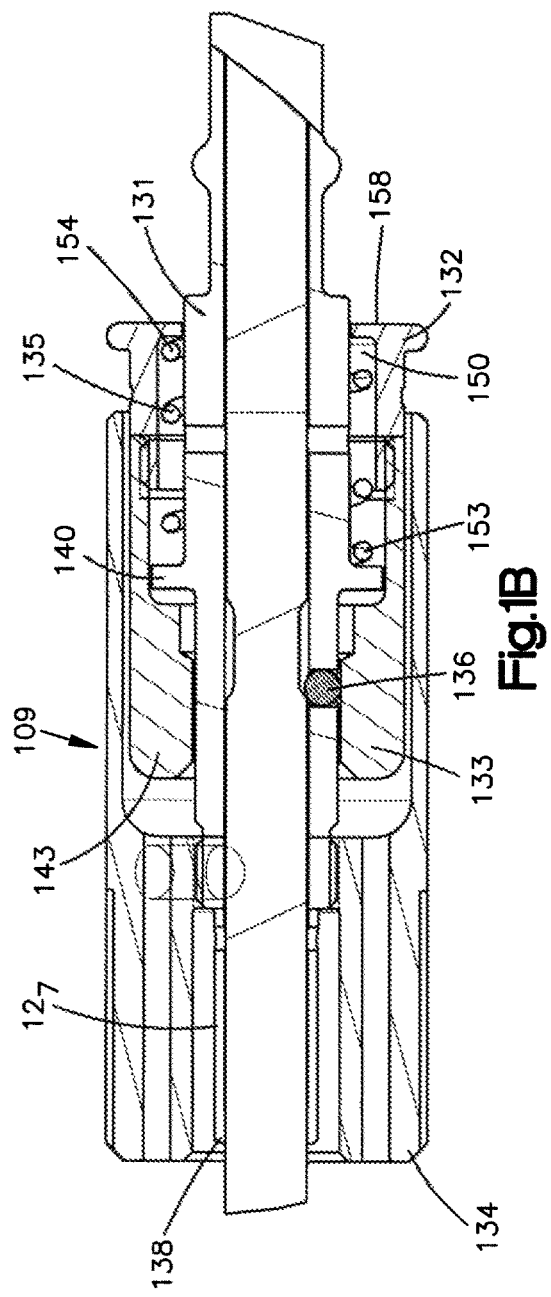
Fig.1A
Fig.1B

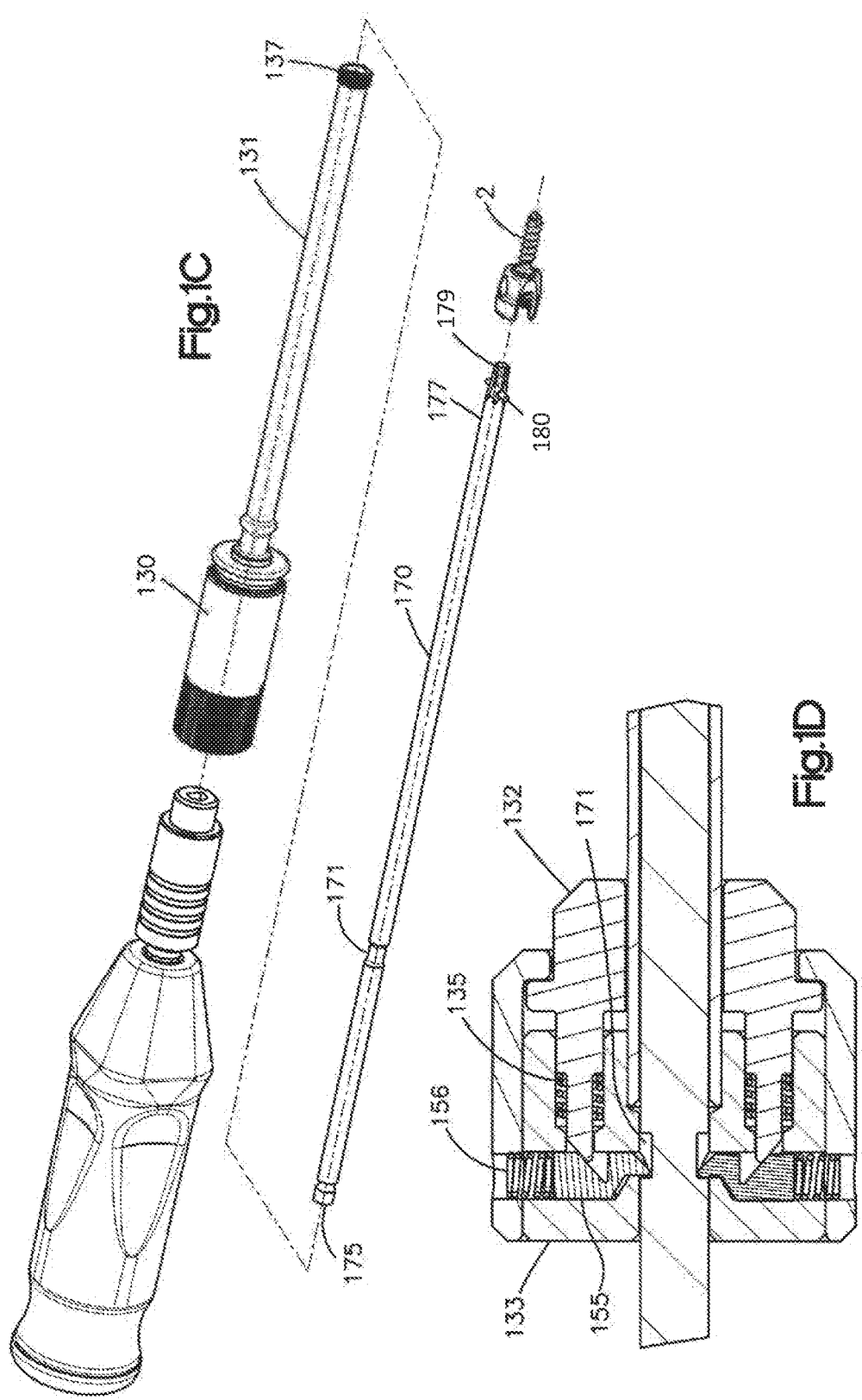

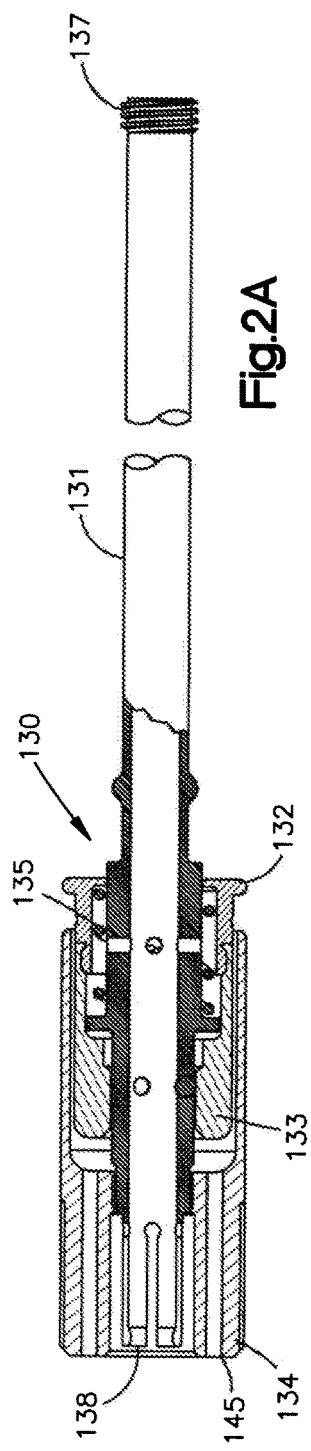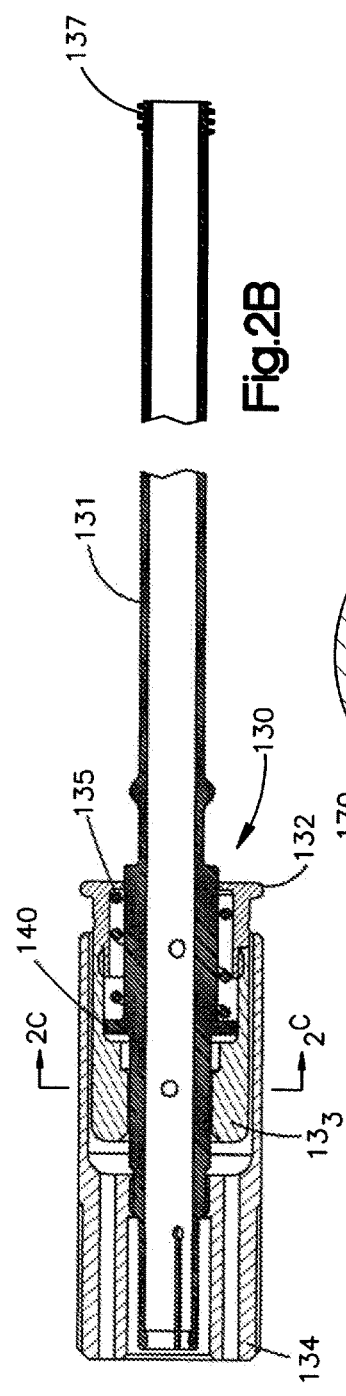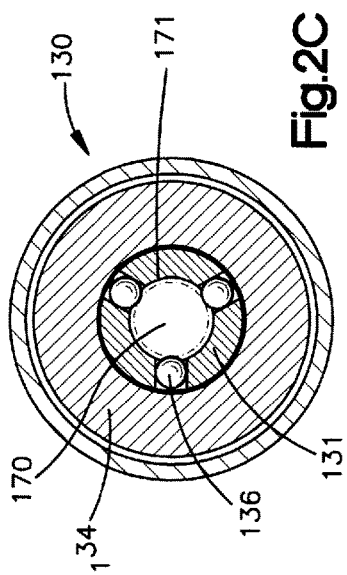

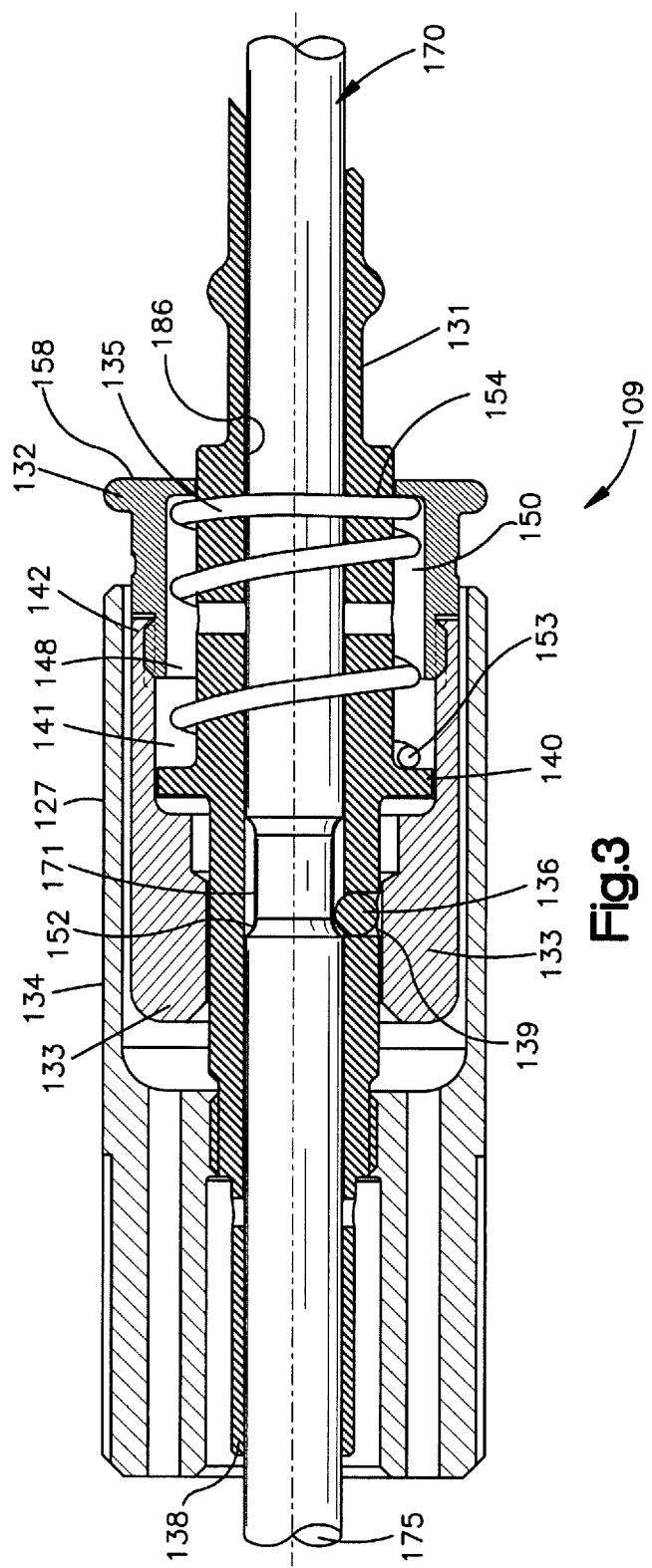

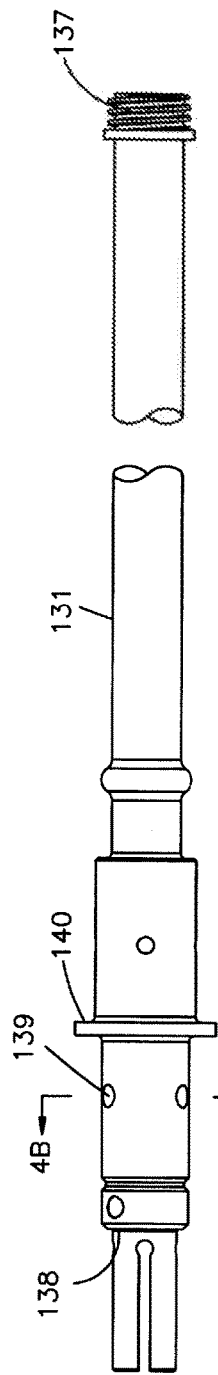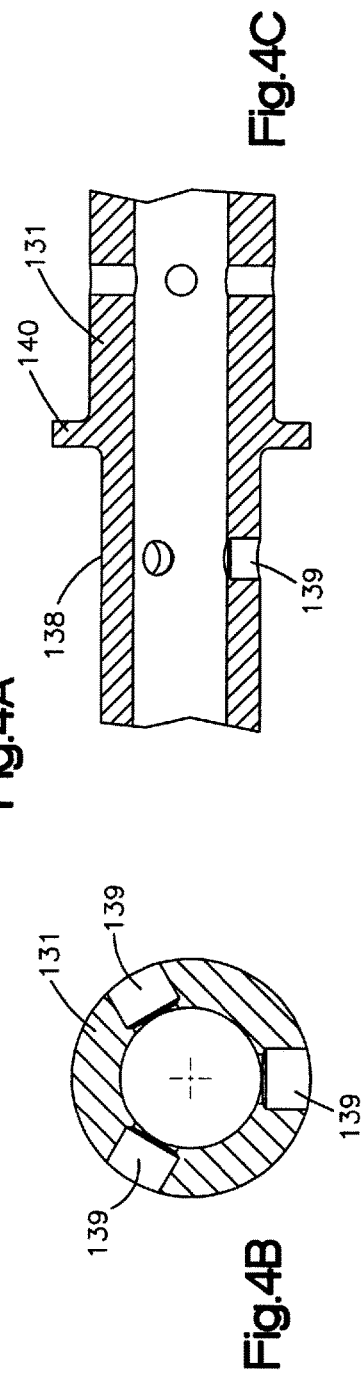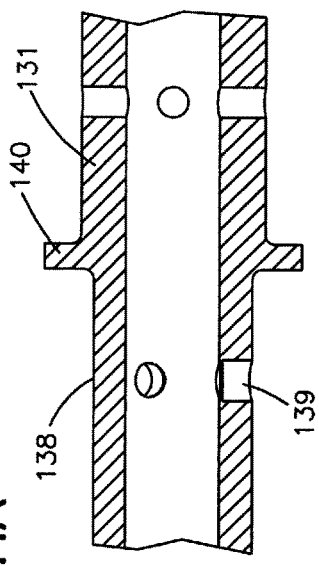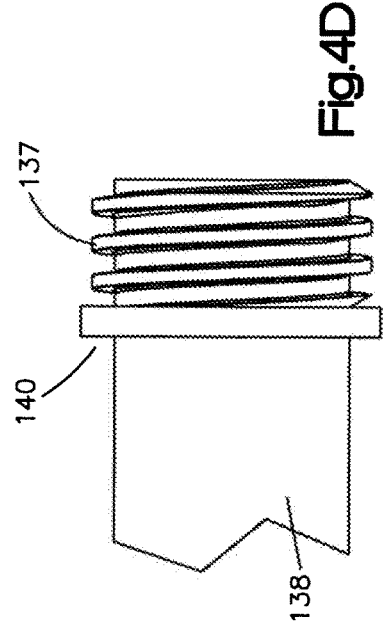

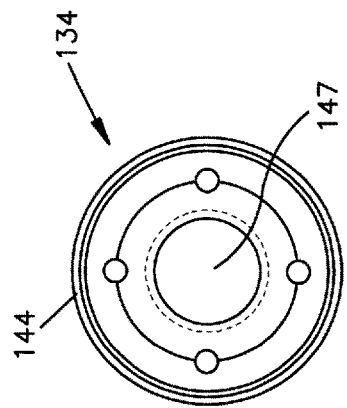
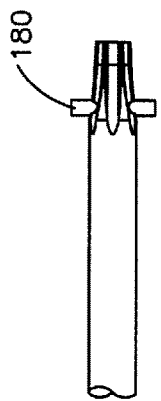
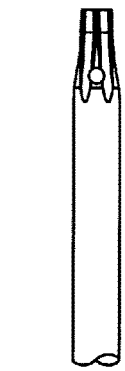
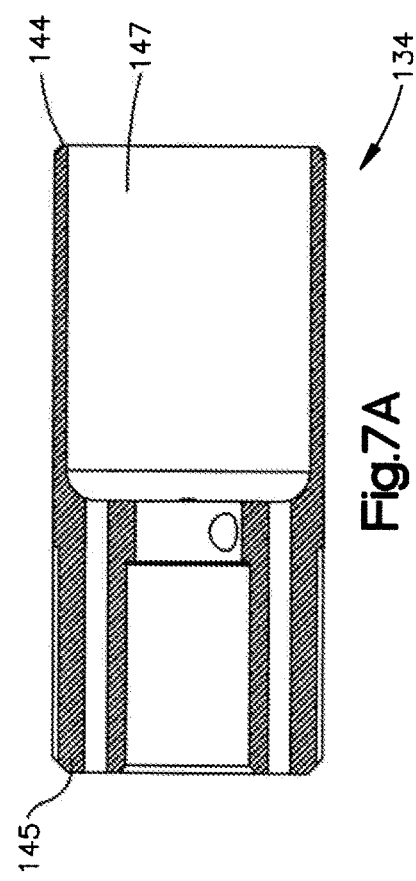
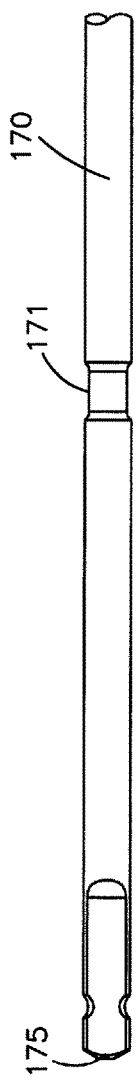

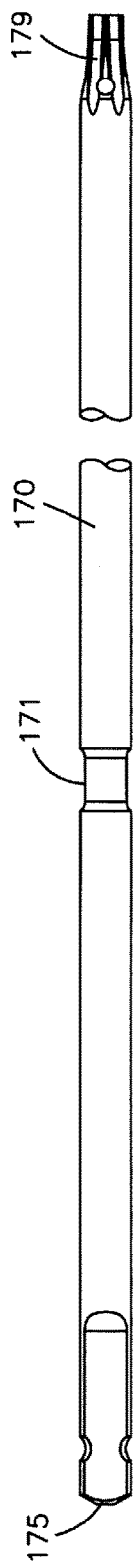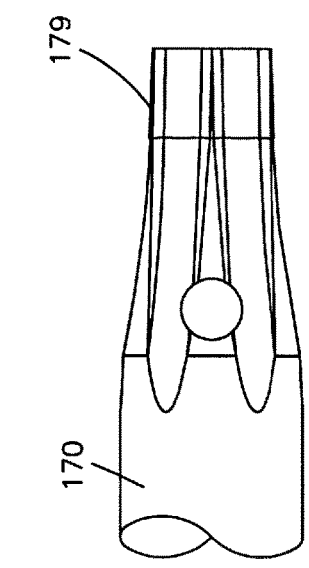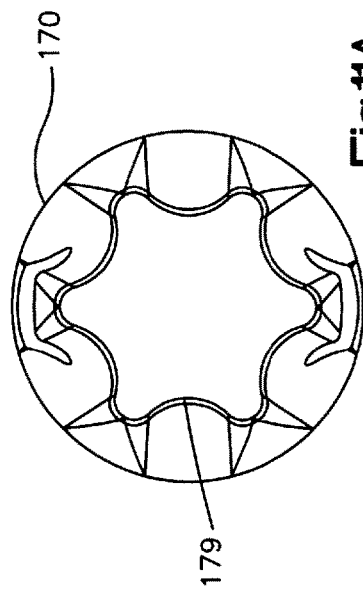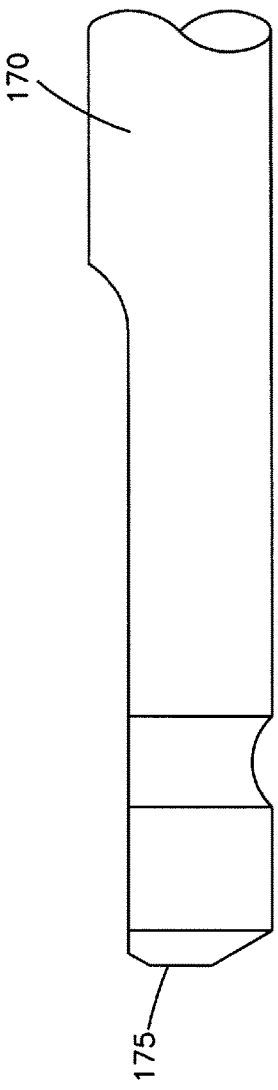

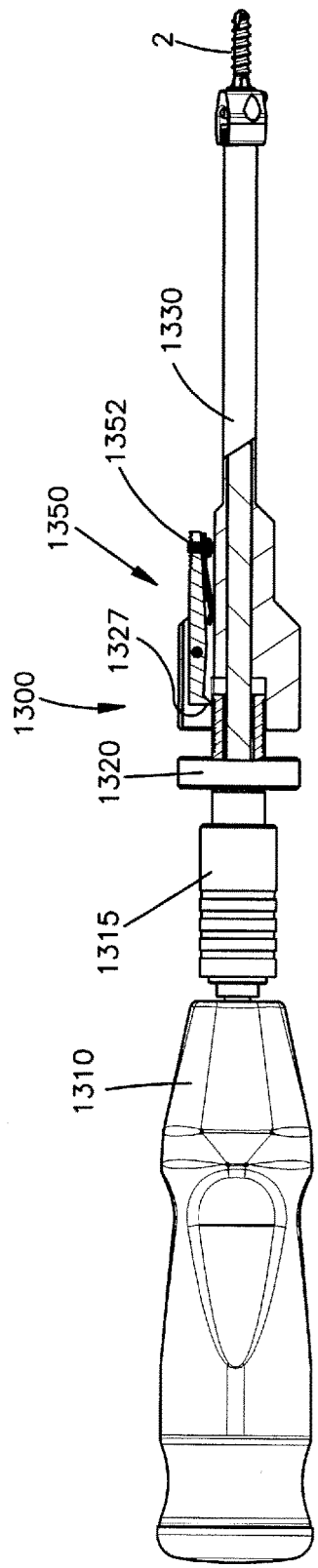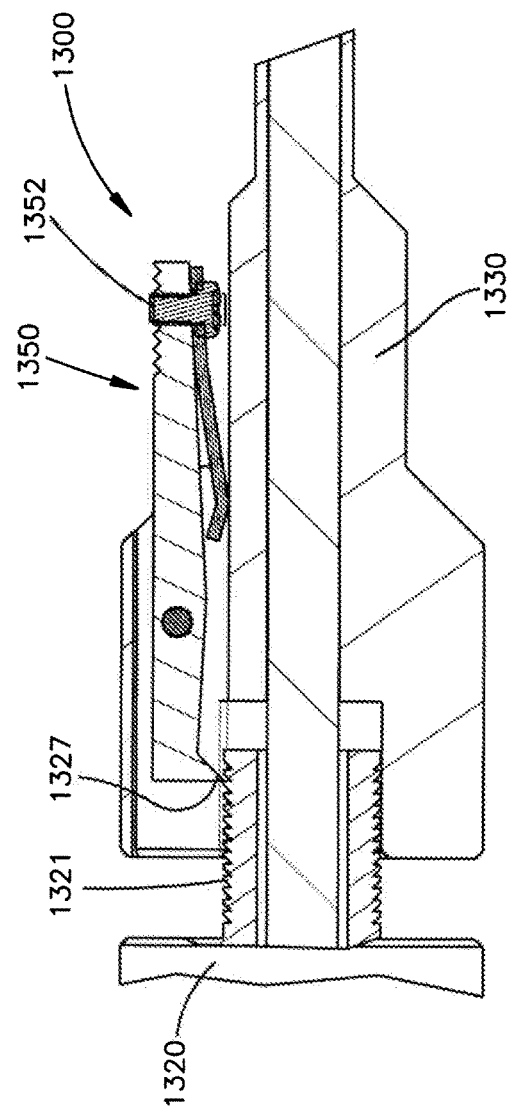
Fig.13A
Fig.13C

PUSH-OFF DRIVER AND METHOD FOR INSERTING BONE SCREWS

CROSS-REFERENCE TO RELATED APPLICATION

This application is a continuation application of U.S. application Ser. No. 15/384,803, filed Dec. 20, 2016, which is a continuation application of U.S. application Ser. No. 14/617,397, filed Feb. 9, 2015, which is a continuation application of U.S. application Ser. No. 13/888,509, filed May 7, 2013, which is a continuation application of U.S. application Ser. No. 11/840,638, filed Aug. 17, 2007, which claims the benefit of provisional application Ser. No. 60/838,797 filed on Aug. 17, 2006, entitled "PUSH-OFF DRIVER AND METHOD FOR INSERTING BONE SCREWS," the entire disclosures of which are hereby incorporated by reference.

FIELD OF INVENTION

The present invention relates to a device and method for inserting screws into a patient.

BACKGROUND OF THE INVENTION

The use of drivers to insert screws, e.g., polyaxial screws, is known in the art. In practice, the polyaxial screw driver connects itself to the polyaxial screw and drives the polyaxial screw into the patient during an implantation procedure.

While in the past, drivers for polyaxial screws have been successful, they have provided numerous difficulties as well. One such problem has arisen during removal of the driver from the polyaxial screw after insertion. In prior art drivers, after a screw has been inserted, the driver may become stuck inside the recess of the screw. This phenomenon is referred to in the art as "sticking". When the driver becomes stuck in the polyaxial screw, it becomes difficult to dislodge the driver from the screw and the surgeon may need to jar the driver to try and disconnect it from the screw. This results in added difficulty to the surgeon. Accordingly, the need exists for a driver that is easily removable from the polyaxial screw allowing more flexibility to the user of the driver and less risk to the patient. The present invention satisfies the foregoing, as well as other needs.

SUMMARY OF THE INVENTION

In view of the above discussion and the shortcomings in the field of drivers for bone screws, the device and method for inserting screws into a patient discussed below seek to overcome such shortcomings. In one embodiment, a push-off driver, (e.g., a posterior cervical push-off driver,) and a method for inserting screws into a patient, (e.g., for posterior fixation of the spine) is disclosed. The driver may comprise a handle, a driver sleeve that is connectable at its distal end to the bone screw; an inner driver that is releasably moveable inside the driver sleeve and has a drive structure to drive the bone screw; and a release mechanism for locking and unlocking the driver sleeve relative to the inner driver. Operation of the release mechanism permits the screw to be pushed off of the inner driver.

In one embodiment, the push-off driver may be a button push-off driver having a handle, an inner driver having one or more recesses, and a threaded driver sleeve having a button mechanism and one or more spheres, where operation of the button mechanism releases the spheres from the recesses. The button mechanism may include a button, an inner driver and a compression spring. The inner driver at its distal end has a drive mechanism which corresponds to a recess or structure on the screw head. Further, the inner sleeve can include one or more bores in which the spheres are seated.

According to one embodiment, a method of releasing a screwdriver from a bone screw includes assembling a push-off driver having a handle, an inner driver having one or more recesses, and a threaded driver sleeve having a button mechanism. Attaching a polyaxial screw to the push-off driver where the polyaxial screw is threaded to the distal end of the outer sleeve and the screw is connected, preferably rigidly, to the inner driver by a cross pin protruding perpendicularly from the distal end of the inner driver, and inserting the polyaxial screw into a patient. When attaching the polyaxial screw to the push-off driver, the threaded driver sleeve advances with respect to the inner driver causing one or more spheres to drop into one or more recesses located on the inner driver. The push-off driver is then detached from the polyaxial screw by unthreading the outer sleeve from the bone screw wherein the one or more spheres engage the one or more recesses to prevent the threaded driver from moving distally and causing the bone screw to disengage from the inner driver. In one embodiment, detaching the bone screw from the push-off driver includes the steps of unthreading the threaded driver sleeve from the polyaxial screw causing the spheres in the recess of the inner driver to back up against the front of the recess preventing the threaded driver sleeve from further moving distally, and continuing to unthread the threaded driver sleeve from the polyaxial screw causing the threaded driver sleeve to push off and release the polyaxial screw from the inner driver.

In another embodiment, the push-off driver comprises a handle, an outer sleeve having a distal end for attaching to a screw, an inner driver where a distal end of the inner driver has a drive mechanism which corresponds to a recess on the screw head, and a cross pin where the cross pin protrudes perpendicularly from the distal end of the inner driver. The driver further includes an upper knurled portion threaded to the proximal end of the outer sleeve, where unthreading the upper knurled portion causes the outer sleeve to release the screw from the inner driver.

In yet another embodiment, a push-off driver for inserting screws comprises a handle, an outer sleeve having a distal end for attaching to a screw, an inner driver where a distal end of the inner driver has a drive mechanism which corresponds to a recess on the screw head. According to one embodiment, the driver includes a ratchet mechanism, and a knurled portion threaded to the proximal end of the outer sleeve where unthreading the knurled portion causes the outer sleeve to release the screw from the inner driver.

BRIEF DESCRIPTION OF THE DRAWINGS

The present invention can be better understood by reference to the following drawings, wherein like reference numerals represent like elements. The drawings are merely exemplary to illustrate certain features that may be used singularly or in combination with other features and the present invention should not be limited to the embodiments shown.

FIGS. 1A-C are perspective and side views of button-push-off embodiment of a push-off driver;

FIG. 1D is a side view of an alternate button push-off embodiment;

FIGS. 2A-C are side and end views of a spring loaded threaded driver sleeve according to one embodiment;

FIG. 3 is a cross view of a spring loaded threaded driver sleeve according to one embodiment;

FIGS. 4A-D are side and end view of an inner sleeve of the threaded driver sleeve of FIGS. 2A-C;

FIGS. 7A-B are side and end views of a trigger housing of the threaded driver sleeve of FIGS. 2B-C;

FIG. 8 is a side view of an inner driver assembly according to one embodiment;

FIG. 9 is a side view of an inner driver assembly according to one embodiment;

FIGS. 10A-B are views of an embodiment of the inner driver of the inner driver assembly of FIGS. 8 and 9;

FIGS. 11A-B are views of an embodiment of the inner driver of the inner assembly of FIGS. 8 and 9;

FIGS. 13A-C are perspective and side views of a ratchet push-off embodiment of a push-off driver.

DETAILED DESCRIPTION OF THE CERTAIN EMBODIMENTS

Figure 6B:
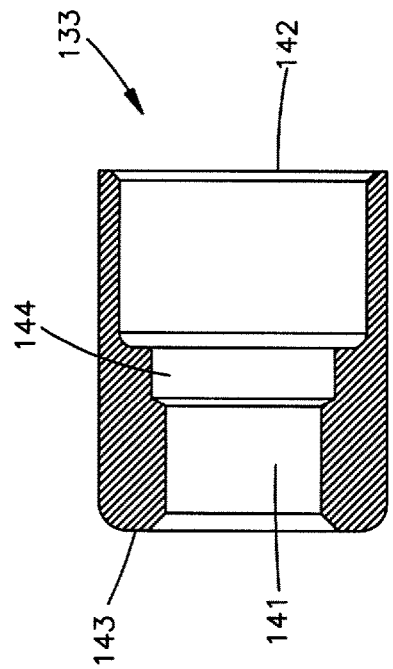
FIGS. 6A-B are side and end views of an outer sleeve of the threaded driver sleeve of FIGS. 2B-C.
Figure 5A:
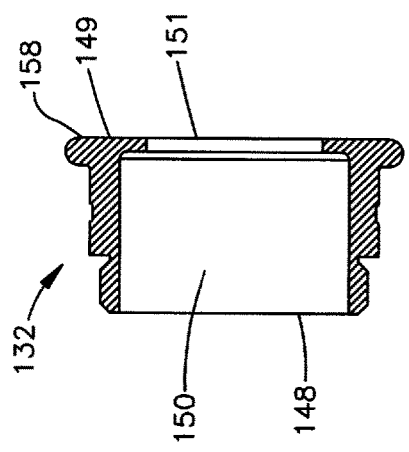
FIG. 5A is a longitudinal cross-section view of a button of the threaded driver sleeve of FIGS. 2A-C.
Figure 6A:
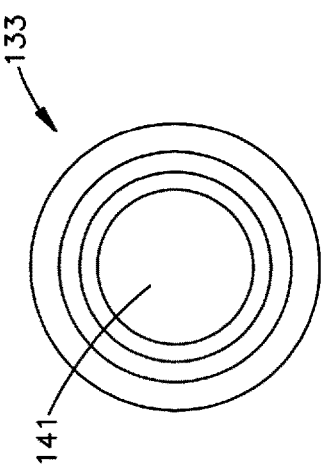

A push-off driver and method for inserting bone screws is described and explained herein. In the following description, for purposes of explanation, certain dimensions, materials and configurations are set forth in order to provide a thorough understanding of the invention. It will be apparent, however, to one having ordinary skill in the art, that the invention may be practiced without these specific details. In some instances, well-known features may be omitted or simplified so as not to obscure the present invention. Additionally, in the specification, the push off driver and the screw to be inserted are generally described as a polyaxial screw driver and a polyaxial screw, but it should be appreciated that aspects of the present invention can be implemented using any bone screw.

Certain embodiments will now be discussed with reference to the aforementioned figures, wherein like referenced numerals will refer to like components. It should be noted that references in the specification to phrases such as "one embodiment" or "an embodiment" means that a particular feature, structure or characteristic described in connection with the embodiment is included in at least one embodiment. The appearances or phrases such as "in one embodiment" in various places in the specification are not necessarily, but can be, referring to the same embodiment.

As can be seen in FIGS. 1A-C, and shown in more detail in FIGS. 2-11, an embodiment of a push-off driver 100 used to insert a screw 2 is shown. In the present embodiment screw 2 is a polyaxial screw, although screws other than polyaxial screws (e.g., monoaxial screws, bone screws etc.) may be used with push-off drivers described herein. As will be discussed in more detail below, push-off driver 100 comprises a handle 160, a spring loaded threaded driver sleeve 130 and an inner driver 170. Push-off driver 100 may be used to thread polyaxial screw 2 into a patient while alleviating the "sticking" phenomenon.

The spring loaded threaded driver 130 comprises a button mechanism 109 which includes an inner driver sleeve 131 (shown in FIG. 4), a button 132 (shown in FIG. 5), a spring 135, an outer sleeve 133 (shown in FIGS. 6A-B) and a trigger housing 134. The trigger housing 134 surrounds and is coaxial with the inner sleeve 131, the outer sleeve 133, the spring 135 and the button 132. The proximal end 145 of the trigger housing 134 is fixed to the proximal end 138 of the inner sleeve 131. The distal end 144 of the trigger housing 134 has a cavity 147 which receives the outer sleeve 133.

Inner driver sleeve 131 is a generally hollow elongated tube having a channel 186 that extends along its longitudinal axis and has one or more bores 139 along its length transverse to the longitudinal axis in which one or more spheres 136 can be seated. Distal to the bores 139 located along its length is a collar 140 which protrudes circumferentially beyond the diameter of the areas proximate the collar and other regions on inner sleeve 131. The button 132 is a cylindrical member (FIG. 5) that has a cavity 150 extending along its length and is located coaxially along the longitudinal axis of the inner sleeve 131 on the inner side of the inner sleeve 131. The button 132 is spring loaded into the button mechanism 109 by being in communication with spring 135 that is similarly located coaxially along the longitudinal axis of the inner sleeve 131 distal from the collar 140.

Outer sleeve 133 (shown in FIGS. 6A-B) has a cavity 141 that extends the entire length of outer sleeve 133. The distal end 142 of the outer sleeve 133 as shown in FIG. 3 overlaps with and is connected to the proximal end 148 of the button 132. The spring 135 is contained within the cavity 141 in the outer sleeve 133 and the cavity 150 in button 132. The proximal end 153 of spring 135 abuts collar 140 on inner sleeve 131 while the distal end 154 of spring 135 abuts against the end wall 158 of the button 132. The collar thus prevents outer sleeve 133 from sliding out of the trigger housing 134 and contracts spring 135. The overlap between the button 132 and the outer sleeve 133 may be secured, for example, by welding, after the compression spring 135 has been assembled onto the inner sleeve 131. The diameter of the cavity 141 may vary along the length of the outer sleeve.

Trigger housing 134 is a hollow tube adjacent to and in communication with the outer sleeve 133. In constructing the button mechanism 109, inner sleeve 131 is inserted through cavity 141 of the outer sleeve 133 and extends past the proximal end 143 of the outer sleeve 133. The proximal end 138 of the inner sleeve 131 which protrudes from the proximal end 143 of the outer sleeve 133 is secured to the proximal end 145 of the trigger housing 134, for example at 127, by threading and/or welding.

Inner driver 170 is an elongated tube that comprises a drive 179 and a cross pin 180 at its distal end 177 and one or more recesses 171 near the proximate end 175 of the inner driver 170. Drive 179 can be one of any number of different types of drives, such as a hex, allen key, phillips, T15, or any other configuration for driving screw 2. The inner driver 170 is configured to be able to fit into threaded driver sleeve 130 at its proximal end 175 when the push-off driver 100 is assembled as will be discussed in more detail below.

Preferred dimensions of the various parts of the push-off driver will now be discussed. It should be appreciated that the dimensions discussed herein are merely exemplary and the present invention is not limited thereby. The inner driver sleeve from its proximal end 138 to the tip of its threaded distal end 137 is preferably about 160 mm to about 200 mm in length, more preferably about 185.5 mm in length. The diameter of the distal end of the inner sleeve 131 proximate to the threaded distal end 137 is about 5.9 mm, and the diameter of the distal end 137 is about 8.5 mm, although other dimensions are contemplated. As was discussed above, distal to the plurality of bores 139 is collar 140 which preferably has a diameter between 10 mm and 15 mm, most preferably about 13 mm, although other dimensions are suitable. The diameter of the proximal end of the inner sleeve 131, which is proximal to the collar 140, is preferably between 6 mm and 9.5 mm about most preferably 8.1 mm, although other dimensions are suitable.

The outer sleeve 133, preferably has a length of about 15 mm to about 25 mm, more preferably about 19.2 mm, and as discussed above has a cavity 141 that extends throughout its entire length. In an embodiment, the diameter of the cavity 141 varies along the length of the outer sleeve 133, whereby the diameter near the distal end 142 of the outer sleeve 133 is approximately 13.3 mm, the diameter towards the middle section of the outer sleeve 133 is approximately 9.6 mm, and the diameter of the cavity 141 at the proximal end 143 of the outer sleeve 133 is approximately 8.2 mm, although other dimensions are contemplated.

The button 132 preferably has a length of about 9.25 mm and has a cavity 150 with a diameter of about 12 mm extending throughout the length of the button 132, although other dimensions are suitable. An opening 151 to the cavity 150 at the distal end 149 of the button 132 preferably has a diameter of about 9.2 mm such that is fits coaxially over the proximal end 138 of the inner sleeve 131, distal to the collar 140. Trigger housing 134, preferably has a length of about 30.5 mm, and has a cavity 147 having an inner diameter of about 14.63 mm such that the outer sleeve 133 is able to fit within the cavity 147. Additionally, the inner driver 170 is preferably about 200 mm to about 240 mm in length, more preferably about 220.5 mm in length.

Assembly and operation of driver 100 will now be described in more detail. To assemble driver 100, spring loaded driver 130 and more specifically, inner sleeve 131 is placed over and on top of proximal end 175 of inner driver 170. The inner driver 170 is slid through the channel 186 of the inner sleeve 131 until the proximate end 175 of the inner driver 170 extends out of the proximal end 138 of the inner sleeve 131. The inner driver 170 is then secured to the handle 160 by threading and or welding the two pieces together or using other means of attachment. As was mentioned above, the inner driver 170 may also include a cross pin/dowel 180 at its distal end 177, or any other configuration which is used to prevent rotation of the polyaxial head relative to the inner driver 170. As the inner driver is slid through the channel 186 of the inner sleeve 131, the distal end of inner sleeve 131 eventually buts up against the cross pin 180 that is attached to the inner driver 170. Inner driver 170 also comprises a drive 179 at its distal end and a recess 171 near the proximal end as can be seen in FIG. 1D.

The threaded driver sleeve 130 is then threaded onto the head of the polyaxial screw 2, using the threaded portion 137. The polyaxial screw 2 and the threaded driver sleeve 130 are then pulled together and the dowel 180 of inner driver 170 engages the polyaxial screw 2 to prevent rotation or toggle of the polyaxial screw 2 when connecting to driver 100. Prior to the driver 100 being threaded onto screw 2, the user of driver 100 depresses button 132 moving outer sleeve 133 proximally enabling spheres 136 to freely move along the bores 139. In one embodiment, there are three bores 139 and three spheres 136 as shown in FIG. 2C, although more or less could be used. In addition, shapes other than spheres 136 can be used as well. More particularly, depressing button 132 moves outer sleeve 133 proximally so that spheres 136 have enough space to protrude beyond bores 139. In this manner the spheres 136 can move into bore 139 so that they no longer protrude into channel 186. Once the screw 2 has been threaded to driver sleeve 130 and the screw 2 is firmly engaged with inner driver 170, button 132 disengages or pops out, which causes spheres 136 to drop into recesses 171 of inner driver 170 and lock driver sleeve 130 and inner driver 170 together. Once attached, the user of the drive (e.g., the surgeon) may secure the polyaxial screw 2 into a bone of a patient.

After the screw has been inserted into the bone of patient, and the user wants to detach the driver 100 from the polyaxial screw 2, he or she begins by unthreading the threaded driver sleeve 130 from the polyaxial screw 2. In prior art systems at the time of unthreading; the driver would have a tendency to "stick" inside the recess of the polyaxial screw 2. To eliminate this "sticking" phenomenon, as the threaded driver sleeve 130 is unthreaded from the polyaxial screw 2, the spheres 136 of the threaded driver sleeve 130, having previously been dropped into the recess 171 of the inner driver 170, "back-up" against the start of the recess 171. This prevents the threaded driver sleeve 130 from further moving backwards (in a proximal direction). Because the threaded driver sleeve 130 is no longer able to move backward as it is unthreaded from the polyaxial screw 2, the threaded driver sleeve 130 forces the polyaxial screw 2 off of the inner driver 170 since the polyaxial screw 2 is firmly implanted in the patient, thereby alleviating the possibility of the inner driver 170 sticking inside the recess of the polyaxial screw 2 as the driver 100 is removed.

There are various alternative methods to using spheres 136 to engage the recess 171 of the inner driver 170. One such method would be to use one or more pins 155 that are spring loaded into outer sleeve 133 utilizing springs 156 as depicted in FIG. 1D. As seen in FIG. 1D, which depicts the pins 155 in recess 171, the spring loaded pins 155 perform the same function as the spheres 136 discussed above. In other words in this embodiment, a spring 156 is used to hold pins 155 near the proximate end of the outer sleeve 133 and the pins 155 would drop into recess 171 at the time that the button 132 is engaged as shown in FIG. 1D. At the time of unthreading, the pins 155 back up against recess 171 to alleviate sticking similar to the way the spheres 136 back up against recess 171 in the previously discussed embodiment. In order to release the pins from the recess 171, the button is disengaged and the pins 155 are removed out of recess 171 towards spring 156.

It should be noted that although the above embodiments are described in terms of utilizing spheres and spring loaded pins, in certain embodiments, other sliding members can be utilized to engage the recesses of the inner driver 170. Alternatively, recesses can be a part of the button mechanism 109 and the spheres 136 or other sliding member be a part of inner driver 170.

Figure 12A:
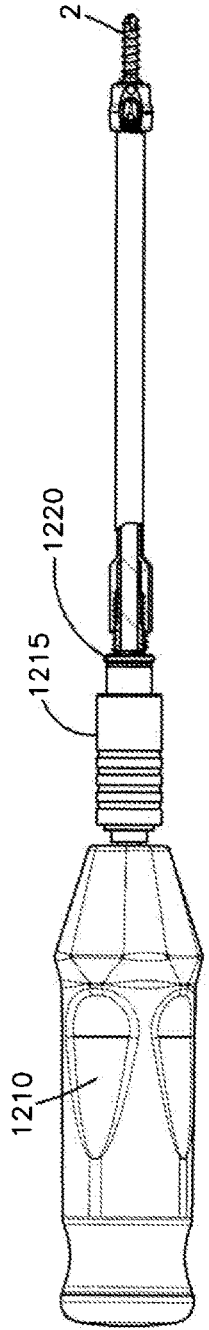
FIGS. 12A-C are perspective and side views of a threaded push-off embodiment of a push-off driver.
Figure 12B:
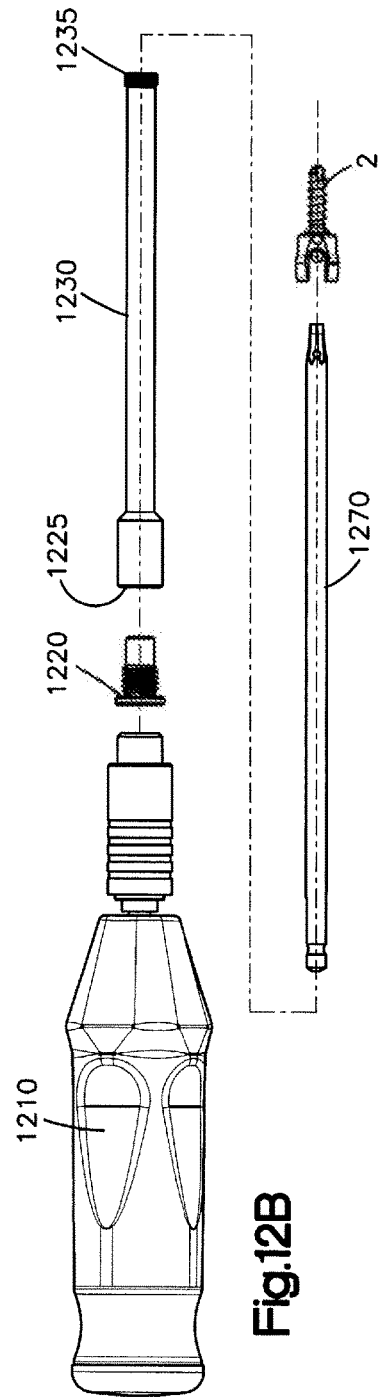
Figure 12C:
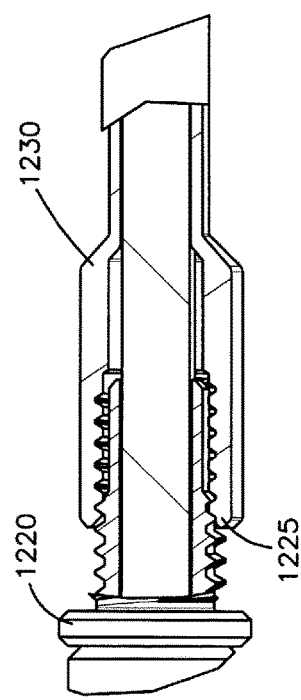

FIGS. 12A-C depict another embodiment of a push-off driver, specifically a threaded push-off driver 1200. The threaded push-off driver 1200 includes handle 1210, an upper knurled portion 1220, an inner driver 1270 having a drive mechanism that corresponds to a recess or other structure on the polyaxial screw head, a cross pin 1280, and an outer sleeve 1230 which has threads 1235 at its distal end. The upper knurled portion 1220 and the outer sleeve 1230 function together, similar to the button mechanism 109 in the embodiment discussed above, to alleviate "sticking" between the inner driver 1270 and the polyaxial screw 2. In one embodiment, the upper knurled portion 1220 is threaded to the proximal end of the outer sleeve 1230.

Operation of the threaded push-off driver depicted in FIGS. 12A-C is performed in a two-step process. First, the push off driver 1200 is assembled by placing outer sleeve 1230 over inner driver 1270. The upper knurled portion 1220 is then threaded into the proximal end 1225 of the outer sleeve 1230 and secured to the distal portion 1215 of the handle 1210. Upper knurled portion 1220 can be secured to handle 1210 using any known methods including welding or screwing the two components together. The inner driver 1270 may also be secured to the handle 1210 by threading and or welding the two pieces together or using other means of attachment.

After driver 1200 has been assembled, polyaxial screw 2 is threaded to the outer sleeve 1230 and locked to inner driver 1270, similar to the way the polyaxial screw 2 is threaded to outer sleeve 130 and locked to inner driver 170 in the embodiment described above. Once the bone screw has been implanted and the user (e.g., the surgeon) wishes to unthread the driver, the user begins to unthread outer sleeve 130 from the bone screw. It is at this point in time, when the outer sleeve 1230 is unthreaded from the polyaxial screw 2 that "sticking" has traditionally occurred. If the user observes that "sticking" is occurring, the user may unthread the upper knurled portion 1220 from the outer sleeve 1230. This is accomplished by the user firmly holding the outer sleeve 1230 and unthreading the upper knurled portion 1220 from the outer sleeve 1230 such that the upper knurled portion 1220 moves proximally towards the handle 1210. This serves the purpose of telescoping the outer sleeve 1230 and effectively shortening the inner driver 1270 since the upper knurled portion 1220 in essence becomes an extension of outer sleeve 1230. Further unthreading of the outer sleeve 1230 from the screw disconnects the inner driver 1270 from the screw 2.

As the upper knurled portion 1220 is moved proximally, it comes into contact with the distal portion 1215 of handle 1210, and the upper knurled portion is no longer able to advance proximally as it is unthreaded from the outer sleeve 1230. Since the upper knurled portion 1220 is unable to advance proximally, continued unthreading of the upper knurled portion 1220 from the outer sleeve 1230 will instead push the outer sleeve 1230 distally which in turn will push the polyaxial screw 2 distally, thereby removing the inner driver 1270 from the recess of the polyaxial screw 2 and alleviating the "sticking" phenomenon. In this embodiment, the outer sleeve 1230 may remain threaded to the polyaxial screw 2 as the upper knurled portion 1220 pushes the inner driver 1270 off of the polyaxial screw 2, or may be unthreaded from the polyaxial screw 2 prior to the upper knurled portion 1220 being unthreaded from the outer sleeve 1230. In either scenario, the unthreading of the upper knurled portion 1220 causes the inner driver 1270 to be pushed off of the polyaxial screw 2.

Figure 13B:
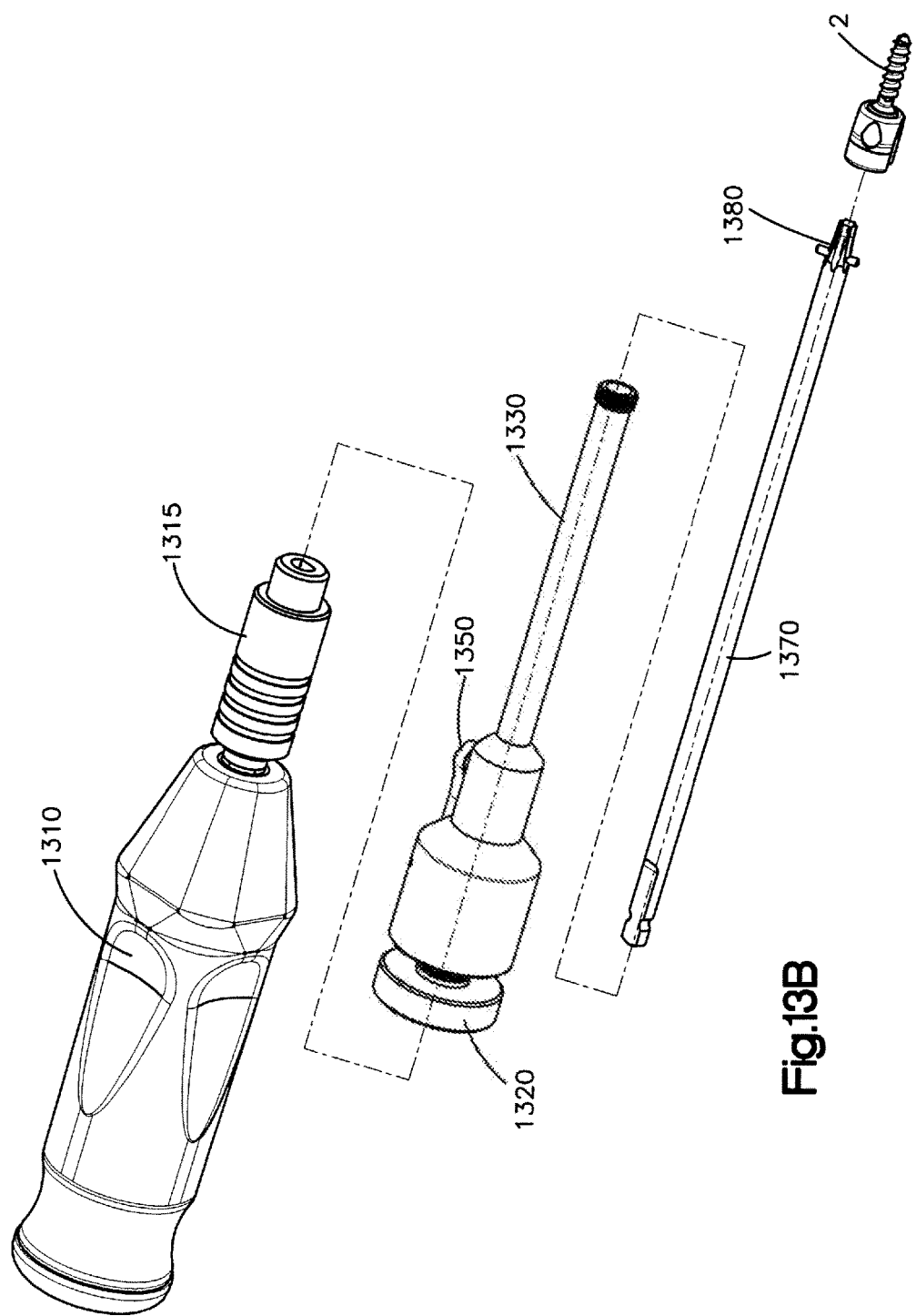

FIGS. 13A-C depict another embodiment of a push-off driver, specifically a ratchet push-off driver 1300. The ratchet push-off driver 1300 includes a handle 1310, a knurled portion 1320, an outer sleeve 1330, an inner driver 1370 having a drive mechanism on its distal end corresponding to a recess or structure on the polyaxial screw head, a cross pin 1380, and a ratchet mechanism 1350, the ratchet mechanism 1350 comprising a trigger 1352, and one or more jaws 1327. The knurled portion 1320 may be fit into a recess 1325 at the proximal end 1326 of the outer sleeve 1330 and the knurled portion 1320 preferably has ridges 1321 which lock into jaws 1327 of the ratchet mechanism 1350, when the ratchet mechanism 1350 is engaged.

Operation of the ratchet push-off driver 1300 as depicted in FIGS. 13A-C is performed in a three-step process. First, the push-off driver 1300 is assembled by placing outer sleeve 1330 over or on top of inner driver 1370. The upper knurled portion 1320 is then inserted into the proximal end 1325 of the outer sleeve 1330 and secured to the distal portion 1315 of the handle 1310. Upper knurled portion 1320 can be secured to handle 1310 using any known methods including welding or screwing the two components together. The inner driver 1270 may also be secured to the handle 1210 by threading and or welding the two pieces together or using other means of attachment.

After the driver 1300 has been assembled, the polyaxial screw 2 is threaded to the outer sleeve 1330, similar to the embodiments described above and the screw is also attached to inner driver 1370 thereby. At that point, the screw is implanted into the patient's bone. When the driver 1300 is to be unthreaded and sticking may occur, the knurled portion 1320 is pulled distally from the outer sleeve 1330 by holding the outer sleeve 1330 and pulling the knurled portion 1320 distally while the ratchet mechanism 1350 is disengaged. Once the knurled portion 1320 comes into contact with the handle 1310, the ratchet mechanism 1350 is released, thus locking the ridges 1325 into the jaws 1327. Once the knurled portion 1320 is locked into the jaws 1327, this prevents the outer sleeve 1330 from further moving backwards (in a proximal direction). Because the outer sleeve 1330 is no longer able to move backward as it is unthreaded from the polyaxial screw 2, the outer sleeve 1330 pushes the polyaxial screw 2 off of the inner driver 1370, thereby alleviating the possibility of the inner driver 1370 sticking inside the recess of the polyaxial screw 2 as the driver 1300 is removed thereby leaving the polyaxial screw implanted properly in the patient.

Another embodiment of a push-off driver is a no button push-off driver (not shown). This embodiment functions very similar to the button push-off driver embodiment discussed above, except that the threaded driver sleeve 130 is longer and rests proximally directly against handle 160. The threaded driver sleeve 130 therefore does not advance distally or proximally when the screw 2 is unthread therefrom. Rather, similar to certain of the embodiments discussed above, as the threaded driver sleeve 130 is unthreaded from the polyaxial screw 2, because the threaded driver sleeve 130 is unable to move proximally as it is unthreaded from the polyaxial screw 2, the threaded driver sleeve 130 forces the polyaxial screw 2 off of the inner driver 170, thereby alleviating the possibility of the inner driver 170 sticking inside the recess of the polyaxial screw 2 as the driver 100 is removed.

Although the present invention and its advantages have been described in detail, it should be understood that various changes, substitutions and alterations can be made herein without departing from the spirit and scope of the invention. Moreover, the scope of the present application is not intended to be limited to the particular embodiments of the process, the assembly, operation, manufacture, composition of matter, dimensions, means, methods, components and steps described in the specification. As one of ordinary skill in the art will readily appreciate from the disclosure, processes, components, machines, manufacture, compositions of matter, dimensions, means, methods, or steps, presently existing or later to be developed that perform substantially the same as the corresponding embodiments described herein may be utilized and are intended to be covered.

What is claimed is:

1. A driver for inserting a bone screw, the driver comprising:
   a handle;
   a driver sleeve that includes a threaded distal end;
   an inner driver that is releasably moveable within the driver sleeve and having a longitudinal axis, a distal end of the inner drive including a drive structure to drive the bone screw, and the inner driver having a recess proximate to a proximal end of the inner driver; and a release mechanism that includes a button, an inner sleeve and an outer sleeve, wherein a first operation of the button releases the outer sleeve to slide about the inner sleeve in a distal direction to lock the driver sleeve relative to the inner driver using an axial locking mechanism that engages within the recess of the inner driver such that a position of the inner driver is fixed relative to the driver sleeve; and wherein a second operation of the button releases the outer sleeve to slide about the inner sleeve in a proximal direction to unlock the driver sleeve relative to the inner driver by disengaging the axial locking mechanism such that the inner driver is moveable relative to the driver sleeve.

2. The driver of claim 1, wherein the inner driver further comprises a cross pin that protrudes perpendicularly from the inner driver's distal end that prevents rotation of the bone screw when connected to the bone screw.

3. The driver of claim 1, wherein the axial locking mechanism comprises a spring-loaded pin that is disposed within the outer sleeve that engages the recess of the inner driver.

4. The driver of claim 3, wherein when locked, the spring-loaded pin of the outer sleeve is movable within the recess of the inner driver in a direction along the longitudinal axis of the inner driver.

5. The driver of claim 3, wherein the spring-load pin engages the recess of the inner sleeve when locked and wherein the spring-loaded pin is removed from the recess when unlocked.

6. The driver of claim 1, wherein the axial locking mechanism comprises a sphere disposed within the inner sleeve that engages a surface of the recess when locked.

7. The driver of claim 6, wherein when locked, the sphere of the inner sleeve is movable within the recess of the inner driver in a direction along the longitudinal axis of the inner driver.

8. The driver of claim 6, wherein the sphere engages the recess of the inner sleeve when locked and wherein the sphere is removed from the recess when unlocked.

9. The driver of claim 1, wherein backward movement of the driver sleeve is prohibited when locked.

10. The driver of claim 1, wherein the driver sleeve is rotatable around the longitudinal axis of the inner driver.

11. The driver of claim 1, wherein when in the locked position, rotation of the driver sleeve longitudinally translates the inner driver with respect to the bone screw, thereby pushing the bone screw off the inner driver.

12. The driver of claim 1, wherein the threaded distal end is adapted to threadably engage a head of the bone screw.

13. An assembly, comprising:

a driver sleeve that includes a threaded distal end;

an inner driver that is received within a bore of the driver sleeve, a distal end of the inner drive including a drive structure to drive a screw, and the inner driver having a recess proximate to a proximal end of the inner driver; and a release mechanism that includes a button, an inner sleeve and an outer sleeve, wherein, upon actuation of the button in a locking mode, the outer sleeve slides about the inner sleeve in a distal direction to lock the driver sleeve relative to the inner driver using an axial locking mechanism that engages within the recess of the inner driver such that a position of the inner driver is fixed relative to the driver sleeve; and wherein upon actuation of the button in unlocking mode, the outer sleeve slides about the inner sleeve in a proximal direction to unlock the driver sleeve relative to the inner driver by disengaging the axial locking mechanism such that the inner driver is moveable relative to the driver sleeve.

14. The assembly of claim 13, wherein the axial locking mechanism comprises a spring-loaded pin that is disposed within the outer sleeve that engages the recess of the inner driver.

15. The assembly of claim 14, wherein when locked, the spring-loaded pin of the outer sleeve is movable within the recess of the inner driver in a direction along the longitudinal axis of the inner driver.

16. The assembly of claim 13, wherein the axial locking mechanism comprises a sphere disposed within the inner sleeve that engages a surface of the recess when locked.

17. The assembly of claim 16, wherein when locked, the sphere of the inner sleeve is movable within the recess of the inner driver in a direction along the longitudinal axis of the inner driver.

18. The assembly of claim 13, wherein backward movement of the driver sleeve relative to the release mechanism is prohibited when locked.

19. The assembly of claim 13, wherein the inner driver further comprises a cross pin that protrudes perpendicularly from the inner driver's distal end.

20. The assembly of claim 13, wherein the driver sleeve is rotatable around the longitudinal axis of the inner driver.

* * * * *